United States Patent [19]
Loo

[11] Patent Number: 5,406,942
[45] Date of Patent: Apr. 18, 1995

[54] SACRAL-INNOMINATE HARNESS

[76] Inventor: Stephen W-M. Loo, P.O. Box 591108, San Francisco, Calif. 94159-1108

[21] Appl. No.: 200,470

[22] Filed: Feb. 22, 1994

[51] Int. Cl.$^6$ .............................................. A61F 5/28
[52] U.S. Cl. ................................ 128/100.1; 128/106.1
[58] Field of Search ................... 128/95.1, 96.1, 98.1, 128/99.1, 100.1, 101.1, 102.1, 105.1, 106.1, 107.1, 112.1; 602/67, 68, 70, 73

[56] References Cited

U.S. PATENT DOCUMENTS

| | | | |
|---|---|---|---|
| 458,127 | 8/1891 | Marvin | 128/100.1 |
| 480,775 | 8/1892 | Marvin | 128/100.1 |
| 717,659 | 1/1903 | Clark | 128/118.1 |
| 792,424 | 6/1905 | King | 602/70 |
| 2,293,998 | 8/1942 | Norwood | 602/67 |
| 2,681,059 | 6/1954 | Dietz | 128/100.1 |
| 3,577,986 | 5/1971 | Regent | 128/107.1 |
| 3,754,549 | 8/1973 | Nelkin | 128/100.1 |
| 4,957,105 | 9/1990 | Kurth | 128/107.1 |

Primary Examiner—Michael A. Brown
Attorney, Agent, or Firm—Douglas E. White; Acronational Law Firm

[57] ABSTRACT

A therapeutic appliance, namely a harness, has a belt, a suspender, a cross-support and an ischial pocket, which harness provides support for the sacroiliac area of a human patient. Use of the harness of this invention will promote resolution of low back pain attributed to sacroiliac strain. The waist belt has two belt ends. The suspender has a strap having two strap ends. The ischial pocket is stitched on the strap, the ischial pocket forming an ischial receiving area. The cross-support is attached to the strap at an acute angle thereto by a fixed cross-support end of the cross-support, the cross-support also having a free cross-support end. A first fastening means is included on the waist belt for fastening one belt end to the other belt end. A second fastening means is included on the strap for fastening the strap ends onto the belt and a third fastening means is included on the cross-support for fastening the free end thereof to the belt.

19 Claims, 5 Drawing Sheets

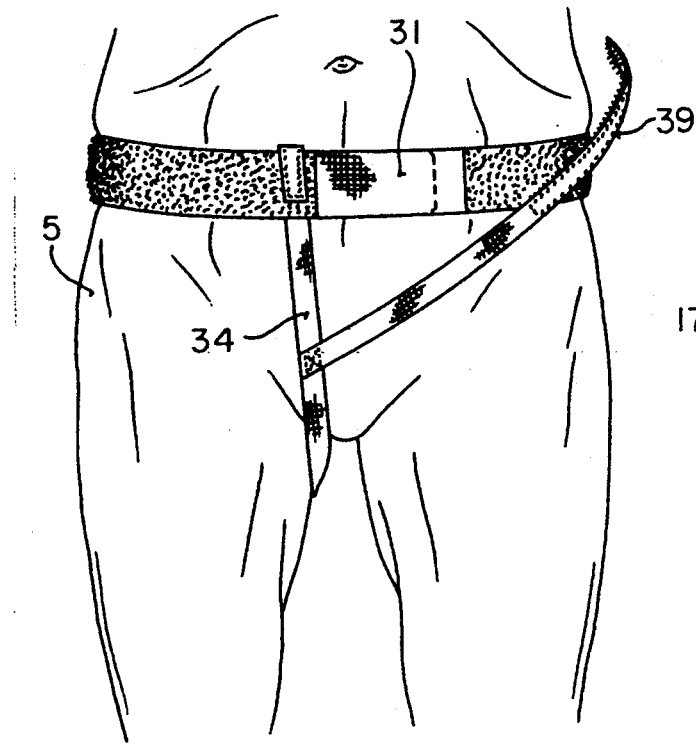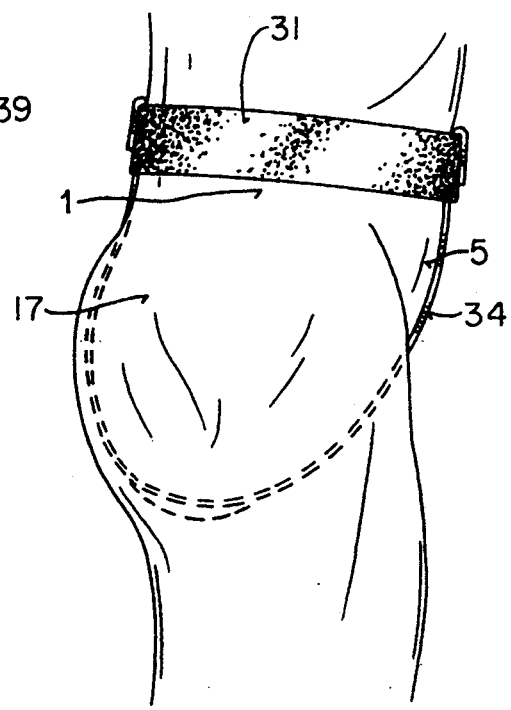
FIG. 2A
FIG. 2B
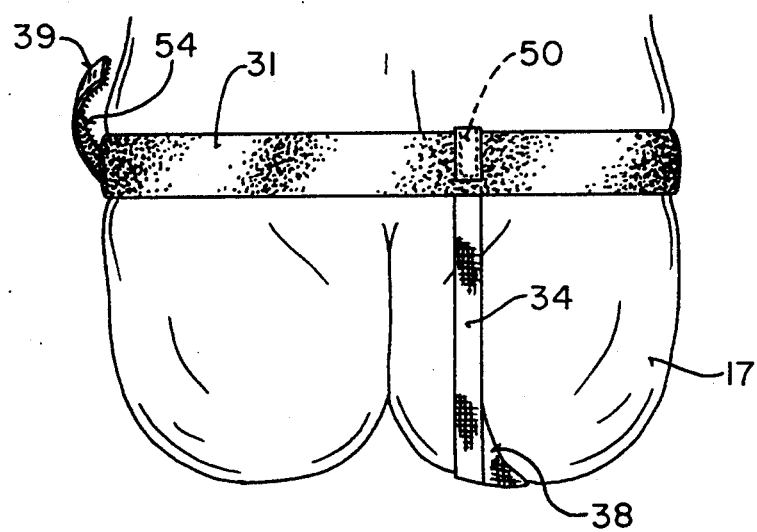
FIG. 2C

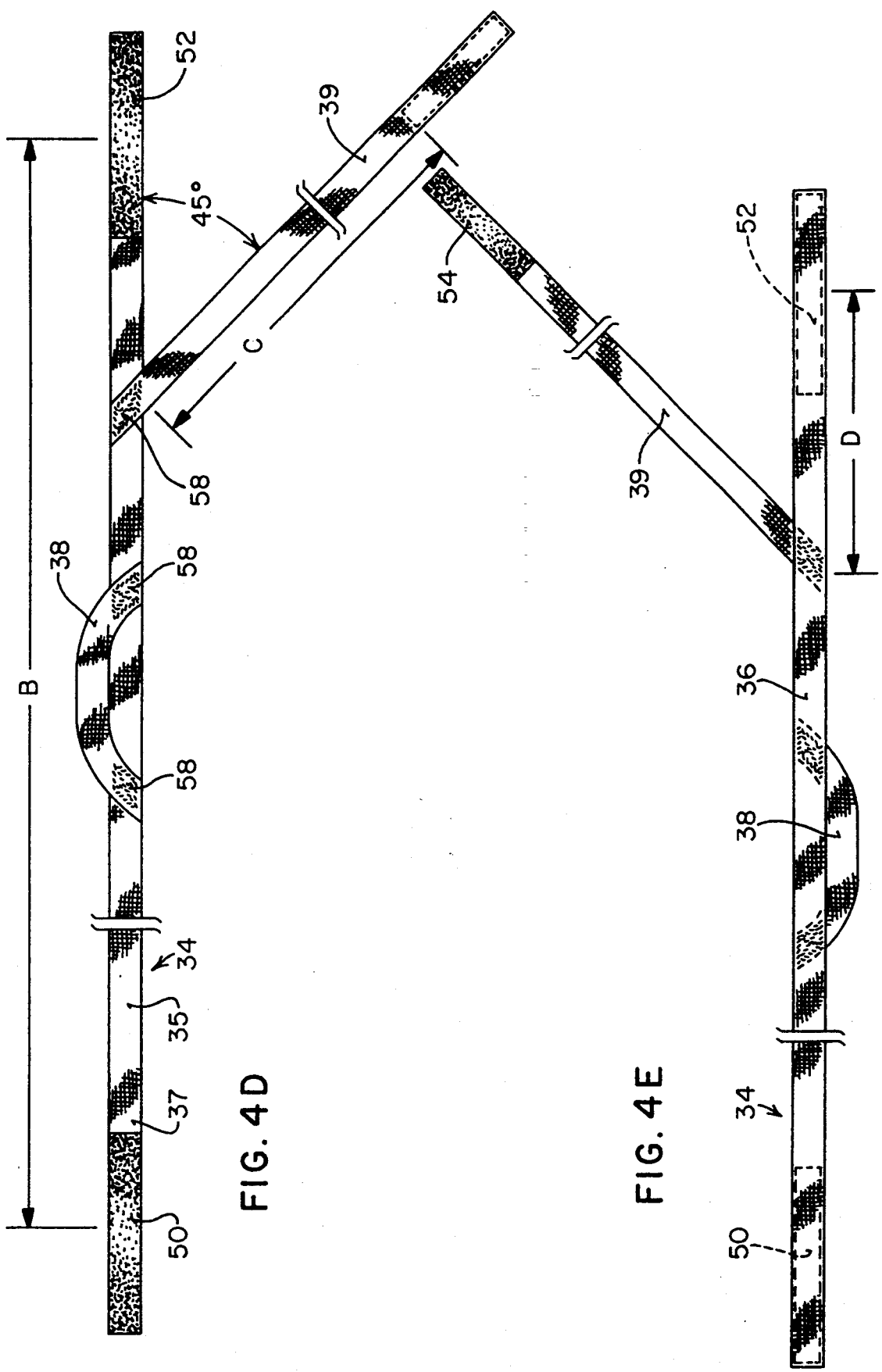

SACRAL-INNOMINATE HARNESS

FIELD OF THE INVENTION

This invention relates to therapeutic support appliances, more particularly to a harness for the support of the sacroiliac area, which harness will promote resolution of low back pain attributable to sacroiliac strain.

BACKGROUND OF THE INVENTION

Low back pain is a common malady and one that causes a significant amount of pain and stress, not to mention economic loss in the form of treatment expense and diminished productivity. Sacroiliac strain (also known as somatic dysfunction of the pelvis, sacroiliac dysfunction, iliosacral impingement syndrome, or sacroiliac subluxation) causes a fair percentage of the low back pain experienced in the general population.

There is no known commercially-available appliance with which to support the sacroiliac area. Therefore, the present invention is proposed to provide support for the sacroiliac area, which support will then promote resolution of low back pain attributable to sacroiliac strain.

Prior developments in this field may be generally illustrated by reference to the following information disclosure statement:

| Patent No. | Patentee | Issue Date |
| --- | --- | --- |
| 39,452 | S. Rawson | Aug. 04, 1863 |
| 3,227,160 | J. Younger | Jan. 04, 1966 |
| 4,622,962 | R. Kauffman | Nov. 18, 1986 |
| 1,868,610 | C. Lane | Jul. 26, 1932 |
| 1,920,648 | C. Lane | Aug. 01, 1933 |
| 3,247,846 | J. Fansler | Apr. 26, 1966 |
| 3,547,117 | J. Smithers | Dec. 15, 1970 |
| 311,570 | J. Cronin | Feb. 03, 1885 |

U.S. Pat. Nos. 3,227,160 and 39,452 teach surgical belts and bandages that have loops which fit across the buttocks. In addition to sanitary protection, these would provide some general support in the pelvic area overall, but not support adapted to alleviate sacroiliac strain.

U.S. Pat. Nos. 1,920,648, 1,868,610 and 4,622,962 teach athletic supporters and a penile support that have straps that come across the buttocks.

U.S. Pat. No. 3,247,846 teaches a shielding device that has two straps suspended from a belt, which device supports surgical dressings.

Adjustable belts and straps are known in the medical field, and are a common feature of the above patents. However, while these items are parts of the present harness, they are not the focus of the invention.

The above patents, in general, were designed to provide "soft" support, for midline structures such as genitalia (U.S. Pat. Nos. 39,452, 4,622,962, 1,868,610, 1,920,648, 3,547,117 and 311,570) or as surgical dressings (U.S. Pat. Nos. 3,227,160 and 3,247,846). None of the designs provide for the firm tethering of the right and left innominates of the pelvis, which is the beneficial focus of the present invention and which is what, in particular, the cross-support strap disclosed herein accomplishes.

Furthermore, the ischial pocket disclosed herein is novel within the art. Its purpose is to lend support to the tethering action of the cross-support strap on the two innominates.

SUMMARY OF THE INVENTION

The present invention is a therapeutic appliance, namely a harness having a belt, a suspender, a cross-support and an ischial pocket, which harness provides support for the sacroiliac area of a human patient. Use of the harness of this invention will promote resolution of low back pain attributed to sacroiliac strain.

As sacroiliac strain is a common cause of low back pain; as osteopathic manipulative therapy helps to realign the structures of the pelvis to relieve this pain; and as there appears to be no commercially available appliance with which to help maintain the proper positional alignments achieved by osteopathic manipulative therapy, the sacral-innominate harness of this invention will provide the proper adjunct with which to promote healing and relief from sacroiliac strain.

FEATURES AND ADVANTAGES

An object of this invention is to provide a sacral-innominate harness apparatus for a human patient having a waist and an ischial area. The harness includes a waist belt having two belt ends. A suspender has a strap having two strap ends. An ischial pocket is stitched on the strap, the ischial pocket forming an ischial receiving area. The harness has a cross-support attached to the strap at an acute angle thereto by a fixed cross-support end of the cross-support, the cross-support also having a free cross-support end. A first fastening means is included on the waist belt for fastening one belt end to the other belt end, the belt having, when fastened in a loop, an interior surface and an exterior surface. A second fastening means is included on the strap for fastening the strap ends onto the belt, and a third fastening means is included on the cross-support for fastening the free end thereof to the belt.

Another object is to provide a harness wherein the second fastening means is a pair of hook and loop fastener pads, one on each strap end, and the third fastening means includes a hook and loop fastener pad on the free cross-support end.

Another object is to provide fourth fastening means comprising one hook and loop fastener pad on the interior surface of the waist belt for mating with the second fastening means of the strap.

Yet another object is to provide a harness wherein the first fastening means is two mating hook and loop fastener pads and the length of the longer of the first hook and loop fastening means pads plus four inches is about twice the length of the fourth hook and loop fastening means pad.

Still another object is to provide such a harness wherein the distance between the point of attachment of the fixed cross-support end and the mid-point of the nearest strap end hook and loop fastener pad is about 0.3 times the distance between the mid-points of the two strap end hook and loop fastener pads.

Another object or feature is that the ischial pocket is an arcuately bent segment of nylon-webbed strapping stitched to about the mid-point of the suspender strap.

Another object is to have the acute angle be substantially 45 degrees.

Another feature is an apparatus which is easy and comfortable to use, unobtrusive in appearance, and suitable for mass production at relatively low cost.

Other novel features which are characteristic of the invention, as to organization and method of operation, together with further objects and advantages thereof will be better understood from the following description considered in connection with the accompanying drawing, in which a preferred embodiment of the invention is illustrated by way of example. It is to be expressly understood, however, that the drawing is for the purpose of illustration and description only and is not intended as a definition of the limits of the invention.

Certain terminology and derivations thereof may be used in the following description for convenience in reference only, and will not be limiting. For example, words such as "upwardly" and "downwardly" would refer to directions in the drawings to which reference is made unless otherwise stated. Similarly, words such as "inwardly" and "outwardly" would refer to directions toward and away from, respectively, the geometric center of a device or area and designated parts thereof. References in the singular tense include the plural, and vice versa, unless otherwise noted.

BRIEF DESCRIPTION OF THE DRAWING

FIG. 2A is a frontal elevation of the harness of this invention installed in place on a human patient in a standing position, FIG. 2B being a left elevation thereof (patient's right) and FIG. 2C being a rear elevation thereof, the latter showing the patient in a seated position;

Figure 1A:
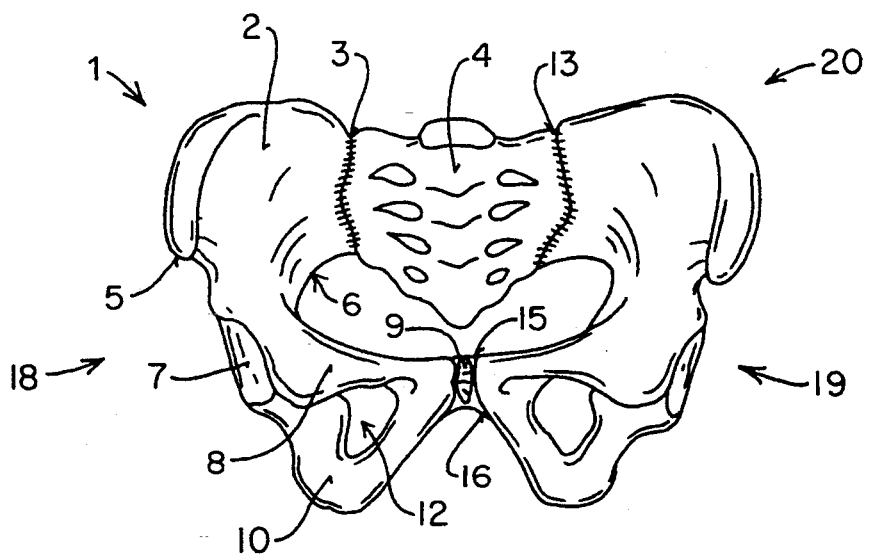
FIG. 1A is a frontal elevation of a human pelvis, within which environment the present invention is employed, FIGS. 1B and 1C being left (patient's right) and rear elevations thereof, respectfully.

| Drawing Reference Numerals | |
| --- | --- |
| 1 | iliac crest |
| 2 | ilium |
| 3 | sacroiliac joint |
| 4 | sacrum |
| 5 | anterior superior iliac spine |
| 6 | greater sciatic notch |
| 7 | acetabulum |
| 8 | pubis |
| 9 | symphysis pubis |
| 10 | ischium |
| 11 | ischial spine |
| 12 | obturator foramen |
| 13 | ventral sacroiliac ligament |
| 14 | dorsal sacroiliac ligament |
| 15 | superior pubic ligament |
| 16 | arcuate pubic ligament |
| 17 | gluteal muscles |
| 18 | right innominate |
| 19 | left innominate |
| 20 | pelvis |
| 30 | sacral-innominate harness |
| 31 | belt of 30 |
| 32 | exterior side of 31 |
| 33 | interior side of 31 |
| 34 | suspender of 30 |
| 35 | exterior side of 34 |
| 36 | interior side of 34 |
| 37 | strap of 34 |
| 38 | ischial pocket of 34 |
| 39 | cross-support of 34 |
| 40 | hook fastener of 33 |
| 42 | loop fastener of 32 |
| 44 | loop fastener of 33 |
| 50 | hook fastener of 34, posterior |

-continued

| Drawing Reference Numerals | |
| --- | --- |
| 52 | hook fastener of 34, anterior |
| 54 | hook fastener of 39 |
| 58 | stitches |
| A | a distance along 31 |
| B | a distance along 34 (B = 0.8 A) |
| C | a distance along 39 (C = 0.4 A) |
| D | a distance along 34 (D = 0.3 B) |
| E | a distance along 31 (E = 0.5 A) |

DESCRIPTION OF A PREFERRED EMBODIMENT

Figure 1B:
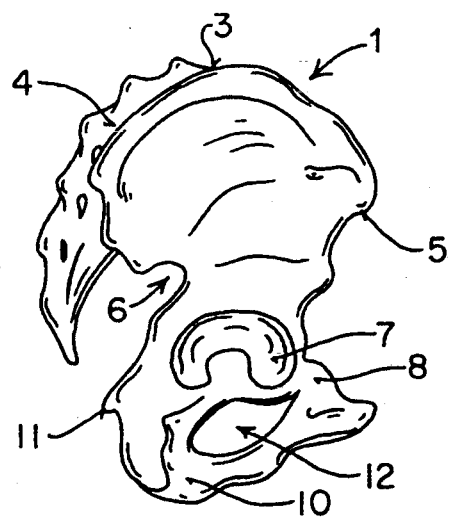
Figure 1C:
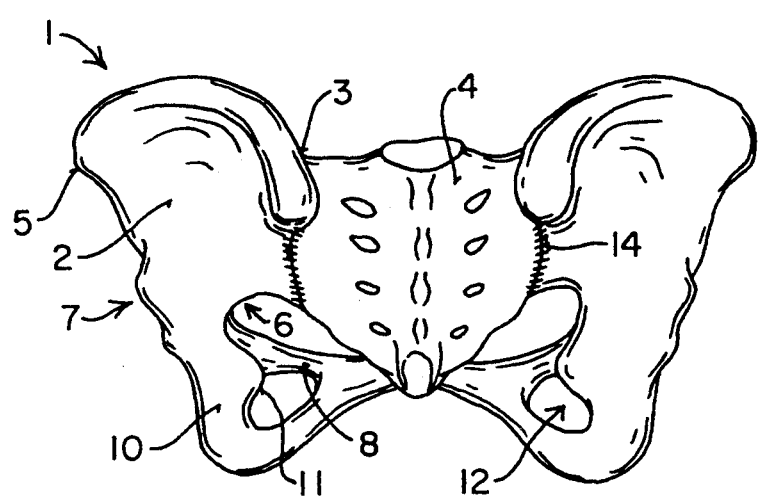
Figure 3:
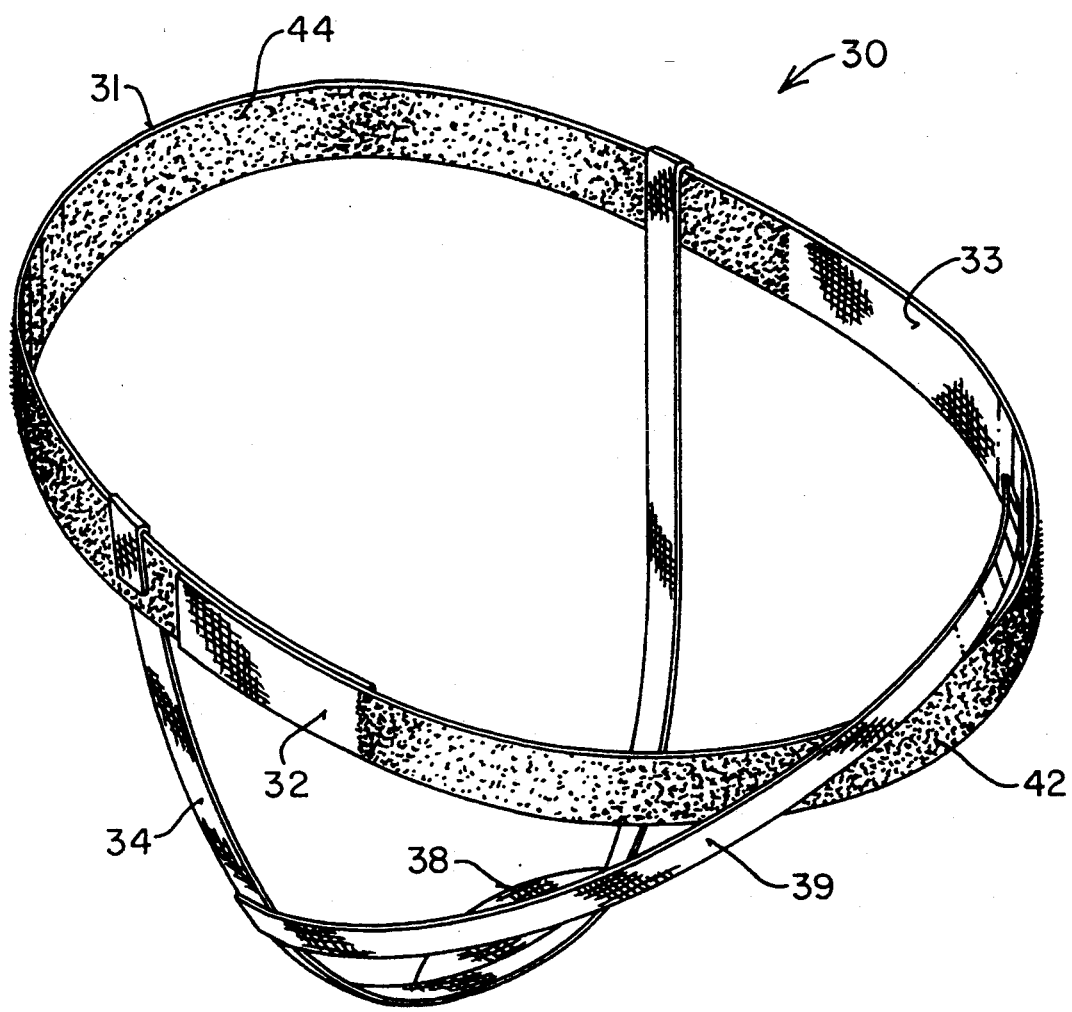
FIG. 3 is a perspective view of the harness in the position it assumes when on a patient.
Figure 4A:
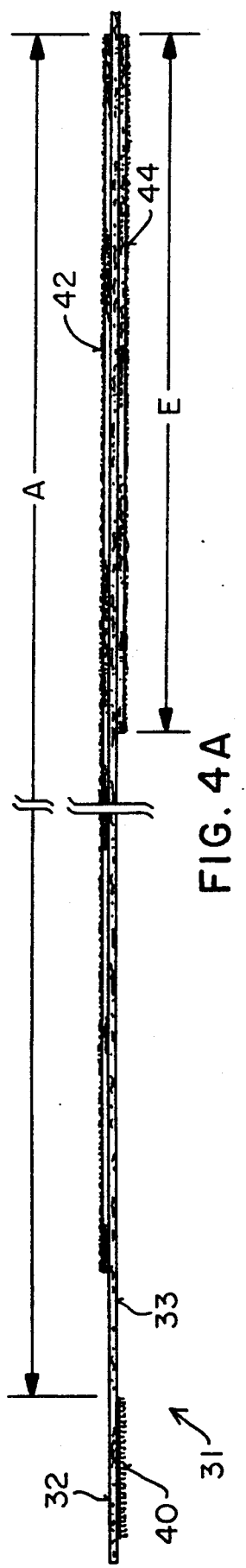
FIG. 4A is a bottom plan view of the belt of the harness, FIGS. 4B and 4C being front and rear elevations thereof, respectively.
Figure 4B:
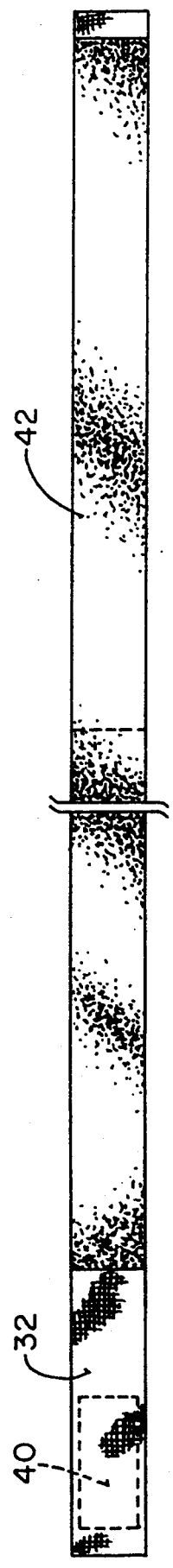
FIG. 4D is a frontal elevation of the suspender of the harness, FIG. 4E being a rear elevation thereof.
Figure 4C:
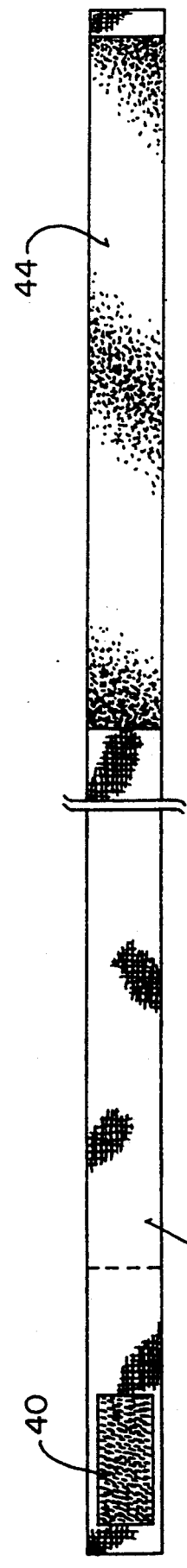

Referring to FIG. 1, there is illustrated therein a pelvis 20 of a human patient, within which environment the sacral-innominate harness 30 of this invention operates. A brief review of the anatomy of the area shows the pelvis 20 as being compromised of three major bones: the sacrum 4, and the two innominates, right 18 and left 19. Each innominate comprises the fusion of the ilium 2, the ischium 10, and the pubis 8. The pelvis is held together by the superior pubic ligament 15, the symphysis pubis 9, and the arcuate ligament 16 anteriorly, and the ventral 13 and dorsal 14 sacroiliac ligaments posteriorly. For purposes of locational reference, also shown in FIGS. 1A–1C are the iliac crest 1, the anterior superior iliac spine 5, the greater sciatic notch 6, the acetabulum 7, the ischial spine 11, the obturator foramen 12 and (FIGS. 2B and 2C) the gluteal muscles 17.

Sacroiliac strain is caused, in general, by patients' inappropriate utilization of body mechanics for activities, or by high impact events such as falls or motor vehicle accidents. Such events place high stress or loads on the sacroiliac ligaments 13, 14. Loaded beyond the point of resiliency, the sacroiliac ligaments become strained in the acute phase, or lax in the chronic phase. This scenario allows the integrity of the sacroiliac joint 3 to be compromised; which, in turn, allows shifts in position between the sacrum 4 and the ilium 2 posteriorly, and, usually, shifts in position between the pubii anteriorly. The most common pattern is the relative anterior rotation of the right innominate 18 onto the sacrum 4. Viewing the patient from the right, one would appreciate a clockwise rotation of the right innominate with respect to the sacrum. This pattern presents, in the acute setting, as sacroiliac ligament strain, impingement, or inflammation of the sacroiliac joint 3, and associated muscle spasms in the surrounding soft tissue structures. In the chronic setting, this pattern presents as pain associated with the iliosacral impingement, and any spasms of the associated soft tissues.

Conventional treatment of rest, ice, anti-inflammatory medication, and physical therapy can control the pain and discomfort. However, experience with osteopathic manipulative therapy reveals this latter modality as being helpful in re-aligning the bones in the proper positional relationship. Once proper positional relationship of the pelvic structure is restored, the pain resolves. Unfortunately, for chronic sufferers, due to loss of resiliency in the sacroiliac ligaments 13, 14, the proper positional relationship of the sacrum and the innominate is difficult to maintain. In these individuals, it does not require a significant stress load to displace the proper positional relationship between the sacrum and the innominate. The sacral-innominate harness 30 of the present invention is believed to properly solve this problem.

Turning to FIGS. 3 and 4A–E, the harness 30 shall be constructed according to waist size measurements, or in predetermined manufacturing sizes-preferably at six inch intervals (e.g. extra small=20" to 26", small=26" to 32", medium=32" to 38", etc.). The harness comprises two major components: the waist belt 31 and the suspender 34. Attached to the strap 37 of the suspender are the ischial pocket 38 and the cross-support 39. Hook and loop fasteners, of the type sold under the brand name VELCRO, comprise fastening means for fastening the major components together, as discussed below. It is to be understood that hook fasteners may be substituted for loop fasteners wherever desired, and vice versa, as long as due consideration is given to maintaining the interconnectability thereof. Furthermore, other types of fastening means might be used in some parts of the invention in substitution for hook and loop fasteners, such as snaps, buckles, buttons, or the like.

The belt 31 is made from leather or sturdy cotton belting material. The width of the belt preferably shall be about two inches. The length of the belt shall be the sum of approximately 6 inches and the human patient's waist size A. In the preferred manufacturing sizes, A shall be the longer length of the size range; e.g. 26" for the "extra small" size mentioned above. On the exterior side 32 of the belt (the side facing out or away from the body when the belt is looped and worn) a loop fastener pad 42 of about two inches in width is attached one inch inwards from the right edge of the belt 31 and runs the length of the belt towards the left edge of the belt for a length of A–4 inches.

On the interior side 33 of the belt (the side facing in toward the body when the belt is worn), a loop fastener pad 44 of about two inches in width is attached one inch inwards from the right edge of the belt, and runs the length of the belt towards the left edge of the belt for a length of $E=\frac{1}{2}A$ inches. A hook fastener pad 40 of about two inches in width is attached to the interior side 33 of the belt 31 about one inch inwards from the left edge of the belt, and runs lengthwise towards the right edge of the belt for a length of about five inches from the left edge of the belt. Hook fastener 40 is about four inches in length.

The suspender 34 and cross-support 39 are made primarily from one-inch wide nylon-webbed strapping material, and ¾-inch wide hook and loop fastener pads.

The suspender 34 preferably measures the length of the sum of eight inches and B inches, where B=0.8 A. On the exterior (outwardly facing) side 35 of the suspender, two pads 50, 52 of hook fastener material, each measuring about seven inches in length, are attached at the two ends of the suspender portion 34, from the edges thereof inwards.

An arcuately bent segment of nylon-webbed strapping at the mid-point of the suspender, measuring about one inch in width, comprises the ischial pocket 38, which pocket forms an ischial receiving and supporting area. The pocket is made by attaching the segment of strapping onto the mid-point of the suspender 34 with stitches 58 in such a manner that the ischial pocket 38 projects laterally out from the right side (when worn-upwardly in FIG. 4D) of the suspender 34. It then runs even with the suspender for one inch or so on either side of the mid-point of the suspender, and then is overlapped onto the exterior (outwardly facing) side 35 of the suspender for a length of about three more inches distal to the mid-point. For added comfort, a cotton or foam pad (not illustrated) may be sewn or glued into the ischial pocket 38 on the interior (inwardly facing) side 36 of the suspender and pocket.

The cross-support 39 is attached to the left side (when worn-downwardly in FIG. 4D) of the suspender 34 on the exterior side 35 at an acute angle to the strap 37 of substantially 45° (or, alternatively, plus or minus perhaps 10°). The point of attachment is D+4 inches from the anterior aspect (when worn-rightwardly in FIG. 4E) of the suspender portion 34, where D=0.3 B. In other words, D is the distance from the point of attachment of the cross-support 39 to the mid-point of pad 52 and B is the distance between the mid-point of pad 50 and the mid-point of pad 52.

The cross-support portion 39 measures the sum of four inches and C, where C=0.4 A. A four inch long, more or less, hook fastener pad 54 is attached to the distal section of the cross-support strap 39 on the interior side thereof.

OPERATION

Proper fitting of the sacral-innominate harness 30 of this invention should be performed by a trained individual, preferably an Osteopath. The harness is to be fit snug on the patient's body. The hook and loop fastener system allows for fine adjustments within the harness.

First, the belt 31 is placed about the patient's waist by mating the interior hook fastener 40 of the belt with the exterior loop fastener 42 thereof. Then, the cross-support 39, with suspender 34, is attached with the hook fastener 50 of the posterior aspect of the suspender slipped between the belt and the body. Any residual length of the posterior aspect of the suspender may be wrapped onto the exterior side 32 of the belt 31. The ischial pocket 38 is wrapped between the patient's legs. It cradles the ischial area 10 of the pelvis 20 on the right. The hook fastener 52 of the anterior aspect of the suspender 34 is slipped between the body and the belt 31 anteriorly.

The suspender 34 is then snugged by adjusting the hook and loop fastener system. Finally, the cross-support portion 39 is brought across the front of the pelvic area and snugly attached to the belt 31 by mating the hook fastener 54 of the cross-support with the exterior 42 and interior 44 loop fasteners of the belt 31.

Once fitted properly, the sacral-innominate harness 30 assists with holding the pelvis 20 in the proper positional relationship. After using osteopathic manipulative therapy to bring about the proper alignment of the innominates 18, 19 and the sacrum 4, the harness 30, notably the cross-support 39, resists any stress or force that might tend to displace the proper positional alignment. By maintaining proper positional alignment, not only will the pain symptoms associated with sacroiliac strain be diminished, but also, this will allow the various support ligaments of the pelvis 20 to heal, remodel and mature, and will regain the integrity of the pelvic rim.

While the above provides a full and complete disclosure of the preferred embodiments of this invention, various modifications, alternative constructions, and equivalents may be employed without departing from the true spirit and scope of the invention. Such changes might involve alternative materials, components, structural arrangements, sizes, operational features or the like. Therefore, the above description and illustrations should not be construed as limiting the scope of the invention which is defined by the appended claims.

What is claimed is:

1. Sacral-innominate harness apparatus for a human patient having a waist and an ischial area, the harness including:
   a waist belt having two belt ends;
   a suspender having
      a planar strap having two strap ends, an ischial pocket on the strap lying substantially within the plane of the strap, the ischial pocket forming an ischial receiving area, the ischial pocket shaped so as to receive and support the ischial area of the patient, and
      a cross-support attached to the strap at an acute angle thereto by a fixed cross-support end of the cross-support, the cross-support also having a free cross-support end;
   first fastening means on the waist belt for fastening one belt end to the other belt end, the belt having, when fastened into a loop, an interior surface and an exterior surface; second fastening means on the strap for fastening the strap ends onto the belt; and third fastening means on the cross-support for fastening the free cross-support end to the belt.

2. The apparatus of claim 1 wherein:
   the second fastening means is a pair of hook and loop fastener pads, one on each strap end, and
   the third fastening means includes a hook and loop fastener pad on the free cross-support end.

3. The apparatus of claim 2 further including:
   fourth fastening means comprising one hook and loop fastener pad on the interior surface of the waist belt for mating with the second fastening means of the strap.

4. The apparatus of claim 1 wherein:
   the acute angle is substantially 45 degrees, and the free cross support end, when fastened to the belt by the third fastening means, is fastened contralaterally with respect to the points of attachment of the strap ends to the belt, when the strap ends are fastened to the belt by the second fastening means.

5. The apparatus of claim 1 wherein:
   the acute angle is between 35 and 55 degrees, and the free cross support end, when fastened to the belt by the third fastening means, is fastened contralaterally with respect to the points of attachment of the strap ends to the belt, when the strap ends are fastened to the belt by the second fastening means.

6. Sacral-innominate harness apparatus for a human patient having a waist and an ischial area, the harness including:
   a waist belt having
      two belt ends,
      an exterior side and an interior side, first and second hook and loop fastener pads on the interior side of the belt, and
      a third hook and loop fastener pad on the exterior side of the belt, the first pad capable of fastening to the third pad so as to form the belt into a closed loop with the exterior belt side facing outward; and
   a suspender having
      a strap having two strap ends,
      fourth and fifth hook and loop fastener pads, one on each strap end for fastening the strap ends onto the second and third pads of the belt,
      an ischial pocket stitched onto the strap, the ischial pocket forming an ischial receiving area, and
      a cross-support attached to the strap at an acute angle thereto at a fixed cross-support end of the cross-support, the cross-support also having a free cross-support end, the free cross-support end having
         a sixth hook and loop pad for fastening the free cross-support end to the third belt pad.

7. The apparatus of claim 6 wherein: the length of the third pad plus four inches is about twice the length of the second pad.

8. The apparatus of claim 7 wherein: the distance between the point of attachment of the fixed cross-support end to the strap and the mid-point of the fifth pad is about 0.3 times the distance between the mid-points of the fourth and fifth pads.

9. The apparatus of claim 8 wherein: the ischial pocket is an arcuately bent segment of nylon-webbed strapping stitched to about the mid-point of the suspender strap.

10. The apparatus of claim 9 wherein: the acute angle is substantially 45 degrees.

11. The apparatus of claim 9 wherein: the acute angle is between 35 and 55 degrees.

12. The apparatus of claim 9 wherein: the waist belt is made of cotton belting material and is about two inches in width.

13. The apparatus of claim 12 wherein: the ischial pocket is padded.

14. The apparatus of claim 13 wherein:
   the first pad is hook fastener material;
   the second pad is loop fastener material;
   the third pad is loop fastener material;
   the fourth pad is hook fastener material;
   the fifth pad is hook fastener material; and
   the sixth pad is hook fastener material.

15. Sacral-innominate harness apparatus for a human patient having a waist and an ischial area, the harness including:
   a waist belt having two belt ends;
   a suspender having
      a strap having two strap ends,
      an ischial pocket on the strap, the ischial pocket forming an ischial receiving area, and
      a cross-support attached to the strap at an acute angle thereto by a fixed cross-support end of the cross-support, the cross-support also having a free cross-support end;
   first fastening means on the waist belt for fastening one belt end to the other belt end, the belt having, when fastened into a loop, an interior surface and an exterior surface,
      the first fastening means being two mating first and second hook and loop fastener pads, a longer one on the exterior surface of the belt and a shorter one on the interior surface thereof;
   second fastening means on the strap for fastening the strap ends onto the belt, namely third and fourth hook and loop fastener pads, one on each strap end;
   third fastening means on the cross-support for fastening the free cross-support end to the belt, the third fastening means including a fifth hook and loop fastener pad on the free cross-support end; and
   fourth fastening means comprising a sixth hook and loop fastener pad on the interior surface of the waist belt for mating with the second fastening means of the strap, the length of the longer of the first and second hook and loop fastener pads plus four inches being about twice the length of the sixth hook and loop fastener pad.

16. Sacral-innominate harness apparatus for a human patient having a waist and an ischial area, the harness including:
  a waist belt having two belt ends;
  a suspender having
    a strap having two strap ends,
    an ischial pocket on the strap, the ischial pocket forming an ischial receiving area, and
    a cross-support attached to the strap at an acute angle thereto by a fixed cross-support end of the cross-support, the cross-support also having a free cross-support end;
  first fastening means on the waist belt for fastening one belt end to the other belt end, the belt having, when fastened into a loop, an interior surface and an exterior stirface;
  second fastening means on the strap for fastening the strap ends onto the belt, namely, a pair of first and second hook and loop fastener pads, one on each strap end; and
  third fastening means on the cross-support for fastening the free cross-support end to the belt, the third fastening means including a third hook and loop fastener pad on the free cross-support end,
    wherein the distance between the point of attachment of the fixed cross-support end and the midpoint of the nearest of the first and second strap end hook and loop fastener pads is about 0.3 times the distance between the mid-points of the first and second strap end hook and loop fastener pads.

17. The apparatus of claim 16 wherein:
  the ischial pocket is an arcuately bent segment of strapping stitched to about the mid-point of the suspender strap.

18. A method of treating sacroiliac strain in a human patient having a waist and an ischial area, including the steps of:
  providing a harness having
    a waist belt,
    a strap having two strap ends, the strap ends connected to the waist belt, and
    an ischial receiving area on the strap;
  placing the waist belt around the patient's waist; and
  placing the patient's ischial area in the ischial receiving area,
    whereby the ischial area is supported by the ischial receiving area, the strap and the waist belt.

19. The method of claim 18 further including the steps of:
  providing a cross support attached to the strap and adjustably attached to the waist belt; and
  adjusting with the cross support the position of the ischial receiving area relative to the patient's waist and ischial area.

* * * * *